US00PP29035P3

(12) United States Plant Patent
Jones

(10) Patent No.: US PP29,035 P3
(45) Date of Patent: Feb. 27, 2018

(54) ***PORTULACA* PLANT NAMED 'PHSFR11-0'**

(50) Latin Name: *Portulaca oleraea*
Varietal Denomination: PHSFR11-0

(71) Applicant: Steve Jones, Santa Monica, CA (US)

(72) Inventor: Steve Jones, Santa Monica, CA (US)

( * ) Notice: Subject to any disclaimer, the term of this patent is extended or adjusted under 35 U.S.C. 154(b) by 0 days.

(21) Appl. No.: 14/999,760

(22) Filed: Jun. 22, 2016

(65) Prior Publication Data

US 2017/0374792 P1 Dec. 28, 2017

(51) Int. Cl.
*A01H 5/02* (2006.01)

(52) U.S. Cl.
USPC ..... Plt./471
CPC ..... *A01H 5/02* (2013.01)

(58) Field of Classification Search
USPC ..... Plt./471
CPC ... A01H 5/02; A01H 5/00; A01H 5/12; A01H 5/0227
See application file for complete search history.

*Primary Examiner* — June Hwu
(74) *Attorney, Agent, or Firm* — Cassandra Bright

(57) ABSTRACT

A new and distinct *Portulaca* cultivar named 'PHSFR11-0' is disclosed, characterized by unique bi-color or tri-color foliage and low, densely growing, spreading plants. The new variety is a *Portulaca*, normally produced as an outdoor garden or container plant.

2 Drawing Sheets

Figure 1:
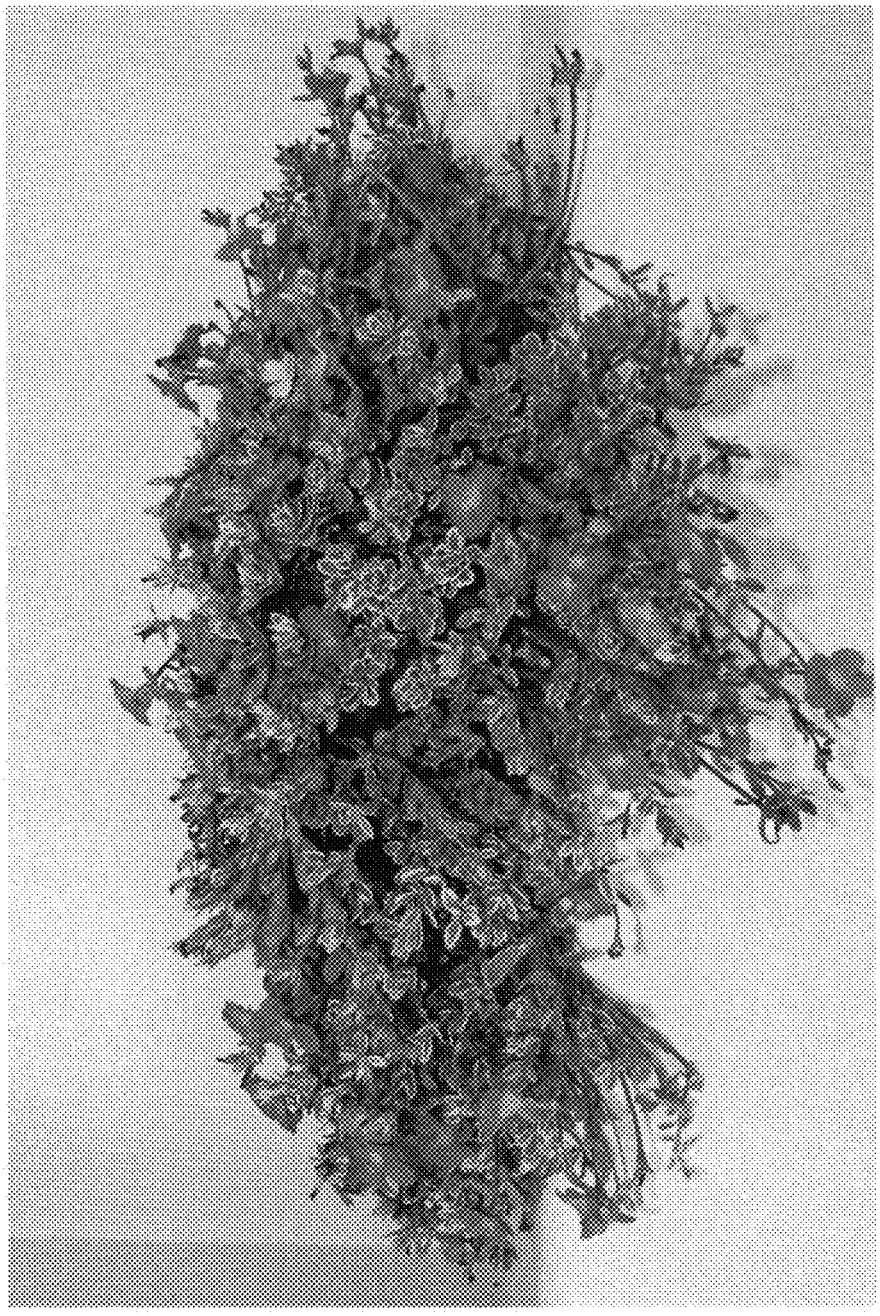

Latin name of the genus and species: *Portulaca oleraea.*
Variety denomination: 'PHSFR11-0'.

BACKGROUND OF THE INVENTION

The new *Portulaca* cultivar is a product of chance discovery by the inventor, Steve Jones, at a commercial greenhouse in Santa Paula, Calif. The breeder discovered an interesting, naturally occurring branch mutation in a planting of unnamed, unpatented *Portulaca oleraea.*

The branch mutation showed bi-color foliage on a plant which was otherwise entirely green in foliage color. This discovery was made during May of 2015.

Asexual reproduction of the new cultivar was first performed by vegetative terminal cuttings. at the same commercial greenhouse in Santa Paula, Calif. in August of 2015. Subsequent propagation and growing the plants over a period of several months shows the variegation pattern is expressed as both bi-color and tricolor. The variegation pattern has shown consistency and stability over the course of three propagative generations.

SUMMARY OF THE INVENTION

The cultivar 'PHSFR11-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'PHSFR11-0' These characteristics in combination distinguish 'PHSFR11-0' as a new and distinct *Portulaca* cultivar:

1. Unique variegated foliage which can be bi-color or tri-color.
2. Low spreading and dense plant habit.
3. Bright pink flowers.

PARENTAL COMPARISON

Plants of the new cultivar 'PHSFR11-0' are similar in most horticultural characteristics to the parent variety. However, the new variety differs in the following:

1. Leaves or the new variety are variegated, foliage of the parent is solid green.
2. Stems of the new variety are flushed pink, stems of the parent are green.
3. Plant vigor of the new variety is less than vigor of the parent.
4. Foliage size of the new variety is smaller than foliage of the parent.

COMMERCIAL COMPARISON

To the best of the inventor's knowledge, the new variety is the only *Portulaca oleracea* plant with variegation and a dense, low growing plant form. Plants of the new cultivar 'PHSFR11-0' can however be compared to the unpatented commercial *Portulaca* 'Cupcakes Grape Jelly'. The two *Portulaca* varieties are similar in most horticultural characteristics; however, the new variety differs in the following:

1. Leaves or the new variety are variegated, foliage of the comparator is solid green.
2. Stems of the new variety are flushed pink, stems of the comparator are green.
3. Plant habit of the new variety is low growing a spreading, while the plant habit of 'Cupcakes Grape Jelly' is semi-upright.

Plants of the new cultivar 'PHSFR11-0' can also be comparable to the unpatented commercial variety can also be comparable to the patented commercial variety *Portulaca* 'SAKPOR001' U.S. Plant Pat. No. 24,528. The two *Portulaca* varieties are similar in most horticultural characteristics; however, the new variety differs in the following:

1. Leaves or the new variety are variegated, foliage of the comparator is solid green.
2. Stems of the new variety are flushed pink, stems of the comparator are green.
3. Plant habit of the new variety is low growing a spreading, while the plant habit of the comparator is semi-upright and semi-mounding.
3. Plant vigor of the new variety is moderate; this comparator has a vigorous growth habit.

BRIEF DESCRIPTION OF THE PHOTOGRAPHS

The accompanying photograph in FIG. 1 illustrates in full color a typical plant of 'PHSFR11-0' grown in a greenhouse, in Santa Paula, Calif. in a 10 inch basket. Age of the plant photographed is approximately 20 weeks from a rooted cutting.

Figure 2:
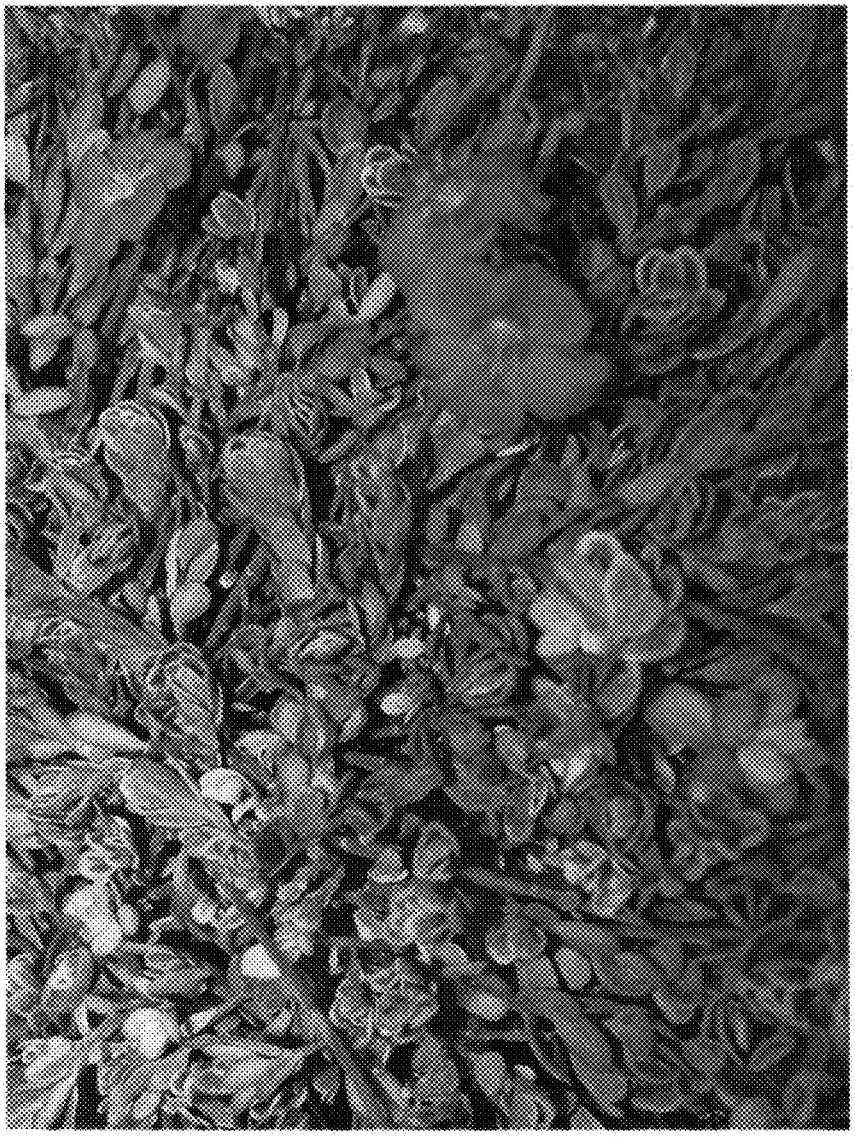

FIG. 2 illustrates a close up of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'PHSFR11-0' plants grown from approximately mid December until mid June in a greenhouse, in Santa Paula, Calif. The growing temperature ranged from 20° C. to 30° C. during the day and from 15° C. to 25° C. during the night. General light conditions are bright, normal sunlight. Measurements and numerical values represent averages of typical plant types.

Botanical classification: *Portulaca* 'PHSFR11-0'.

PROPAGATION

Time to initiate roots: About 20 days at approximately 20 to 22° C.

Time to initiate roots: 10-14 days at approximately 18-21° C.

Root description: Fibrous, spreading and dense.

PLANT

Growth habit: Low and spreading, semi-trailing and dense.

Pot size of plant described: 6 inch.

Height: Approximately 5 cm.

Plant spread: Approximately 30 cm.

Growth rate: Slow to moderate.

Branching characteristics: Very free-branching.

Branching characteristics: Tight, compact, dense branching.

Length of primary lateral branches: 12 cm.

Diameter of lateral branches: 0.3-0.4 cm.

Quantity of primary lateral branches: About 25.

Characteristics of primary lateral branches:

- *Form*.—Round with approximately 4 to 6 ridges.
- *Diameter*.—Approximately 0.4 cm.
- *Color*.—Near RHS Greyed-Red 182B and Greyed-Purple 186B. Both colors present in flushes. Closest to the stem apex, RHS Yellow-green 145C.
- *Texture*.—Glabrous.
- *Strength*.—Flexible.

Internode length: Average range 1.0 to 1.5 cm.

FOLIAGE

Leaf:

- *Arrangement*.—Alternate.
- *Quantity*.—Approximately 16 to 22 per branch.
- *Average length*.—Average range from 1.8 to 2.8 cm.
- *Average width*.—Average range from 1.0 to 1.7 cm.
- *Shape of blade*.—Oblanceolate to nearly spatulate as foliage ages.
- *Apex*.—Rounded.
- *Base*.—Acuminate.
- *Margin*.—Entire.
- *Texture of top surface*.—Smooth.
- *Texture of bottom surface*.—Smooth.
- *Pubescence*.—Absent.
- *Aspect*.—Flat, angle of attachment about 75°.
- *Color*.—Emerging foliage upper side: Near RHS Yellow 2D. Infrequently flushed Red-Purple 61C. Emerging foliage under side: Near RHS Yellow 2D. Infrequently flushed Red-Purple 61C. Young foliage upper side: RHS Green 137C, margin Yellow 2C. Occasional marginal flush near Red 54C, and fine marginal edge near Red-Purple 61B and N66A. Young foliage under side: RHS Green 138B, margin Yellow 5D. Often margins may be flushed Red-Purple 61C. Less frequently entire leaf blade may be flushed Red-Purple 63C. Drier conditions and higher light appear to increase the Red-Purple flushing. Mature foliage upper side: RHS Green 137B, margin Yellow 8C and 8D. Marginal flush near Red 54C, and fine marginal edge near Red-Purple 61B and N66A. Mature foliage under side: RHS Green 138B, margin Yellow 8C and 8D. Marginal flush near Red-Purple N66C. Fine marginal edge near Red-Purple N66A.
- *Venation*.—Indistinguishable from leaf blade.
- *Petiole*.—Absent.

FLOWER

Natural flowering season: Spring to Autumn in Santa Paula, Calif.

Days to flowering from rooted cutting: About 6 to 8 weeks

Inflorescence and flower type and habit: Terminal inflorescence. Single rotate flower.

Rate of flower opening: 3 to 5 days from bud to fully opened flower.

Flower longevity on plant: Approximately 2 to 4 days.

Persistent or self-cleaning: Self cleaning.

Bud:

- *Shape*.—Narrowly conical.
- *Length*.—Approximately 1.0 cm.
- *Diameter*.—Approximately 0.5 cm.
- *Color*.—Bud base: RHS Green 137B with Yellow 4D. Apex flushed N66B and N66C.

Flower size:

- *Diameter*.—3.5 cm.
- *Height*.—1.5 cm.

Corolla/petals:

- *Arrangement*.—Single flower with 5 distinct petals fused at base.
- *Length*.—Approximately 1.8 cm.
- *Width*.—Approximately 1.5 cm.
- *Quantity*.—5 petals.

*Texture*.—Glabrous.
*Apex*.—Rounded, with shallow rounded lobes.
*Shape*.—Obovate.
*Margin*.—Entire.
*Color*.—When opening: Upper surface: RHS Red-Purple N74A. Base colored near Yellow 2B. Lower surface: RHS Red-Purple N74B. Very small portion of base colored near Yellow 2B. Fully opened: Upper surface: RHS Red-Purple N74A, but much brighter. Base colored near Yellow 2C. Lower surface: RHS Red-Purple N74A and N74B. Base colored near Yellow 2B.

Calyx/sepals:
*Quantity per flower*.—2 Sepals per flower.
*Shape*.—Deltoid, elliptic with pointed tip.
*Length*.—0.7 cm.
*Width*.—0.5 cm.
*Apex*.—Acute.
*Base*.—Fused.
*Margin*.—Entire.
*Texture*.—Glabrous all surfaces.
*Color*.—Upper Surface: RHS Yellow-Green 144A and Yellow 8D. Lower Surface: RHS Yellow-Green 144b and Yellow 8D.

Peduncle:
*Length*.—Approximately 0.5 cm.
*Diameter*.—Approximately 0.3 cm.
*Color*.—RHS Yellow-Green 144C.
*Texture*.—Glabrous.

Fragrance: No.

REPRODUCTIVE ORGANS

Stamens:
*Number*.—Approximately 50.
*Filament length*.—Approximately 0.2 cm.

Anthers:
*Shape*.—Oval, bi-lobed.
*Length*.—Less than 0.5 mm.
*Color*.—RHS Yellow 8C.
*Pollen*.—Color: Near RHS Yellow-Orange 23A. Quantity: Moderate.

Pistil:
*Number*.—1 per flower.
*Length*.—1.1 cm.
*Style*.—Length: 0.8 cm. Color: Near RHS Yellow 8C.
*Stigma*.—Shape: 5 branched stigma. Color: Near RHS Red-Purple 67A. Ovary Color: Near RHS Yellow-Green 145D.

OTHER CHARACTERISTICS

Seeds and fruits: Fruits are egg-shaped 4 mm long with a conical shape top. Seeds are dark grey to black, minute sphere, less than 1 mm. Too small to correctly identify R.H.S. color.

Disease/pest resistance: Neither resistance nor susceptibility observed. *Portulaca* is not typically susceptible to many diseases and pests. The most common diseases being typical root rots from over watering, or black stem, *Dichotomophthora portulacae*. The most common pest of *Portulaca* is Aphid.

Temperature tolerance: Will not tolerate temperatures below 7° C. High temperature tolerance to at least 40° C.

What is claimed is:

1. A new and distinct cultivar of *Portulaca* plant named 'PHSFR11-0' as herein illustrated and described.

* * * * *